(12) United States Patent
Zhang (10) Patent No.: US 7,819,018 B2
(45) Date of Patent: Oct. 26, 2010

(54) TESTING APPARATUS OF MECHANICAL ENDURANCE

(75) Inventor: Bing-Jun Zhang, Shenzhen (CN)

(73) Assignees: Hong Fu Jin Precision Industry (ShenZhen) Co., Ltd., Shenzhen, Guangdong Province (CN); Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 230 days.

(21) Appl. No.: 12/257,360

(22) Filed: Oct. 23, 2008

(65) Prior Publication Data

US 2009/0249886 A1 Oct. 8, 2009

(30) Foreign Application Priority Data

Apr. 8, 2008 (CN) .......................... 2008 1 0300868

(51) Int. Cl.
*G01N 3/00* (2006.01)
(52) U.S. Cl. ....................................................... 73/788
(58) Field of Classification Search .................. 73/788
See application file for complete search history.

(56) References Cited

U.S. PATENT DOCUMENTS 4,709,605 A * 12/1987 Clark ............................. 83/23
4,776,205 A * 10/1988 Brooks et al. ................. 73/37.9
6,383,057 B1 * 5/2002 Bartlett et al. ................. 451/7

* cited by examiner

*Primary Examiner*—Lisa M Caputo
*Assistant Examiner*—Octavia Davis
(74) *Attorney, Agent, or Firm*—Zhigang Ma (57) ABSTRACT

An apparatus for testing mechanical endurance includes a bed for installing a workpiece, a clipping imitator capable of clipping a clipping ring of the workpiece, a hinging imitator capable of engaging with a hinge of the workpiece thereby making the workpiece tend to rotate, a cam, an oscillating rod following the cam, a pressure sensor capable of receiving pressure from the workpiece, a first arithmometer for taking count of pressure dropping the pressure sensor detects, and a second arithmometer for taking count of cam cycles. The oscillating rod includes first and second arms. The second arm engages the cam and can impel the clipping imitator to detach from the clipping ring. The first arm can press the workpiece down. In a cam cycle, if the workpiece does not break, the count of the first arithmometer equals to the count of the second arithmometer; or if breaks, the counts are different.

18 Claims, 11 Drawing Sheets

TESTING APPARATUS OF MECHANICAL ENDURANCE

BACKGROUND

1. Field of the Invention

The present invention relates to testing apparatuses and, more particularly, to a testing apparatus for testing mechanical endurance.

2. Description of Related Art

In mechanical engineering, mechanical endurance testing is an important test for quality control of the products. Inventive testing devices for mechanical endurance are always desired in terms of improving the effectiveness of the testing process and increasing productivity.

DETAILED DESCRIPTION

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

Figure 1:
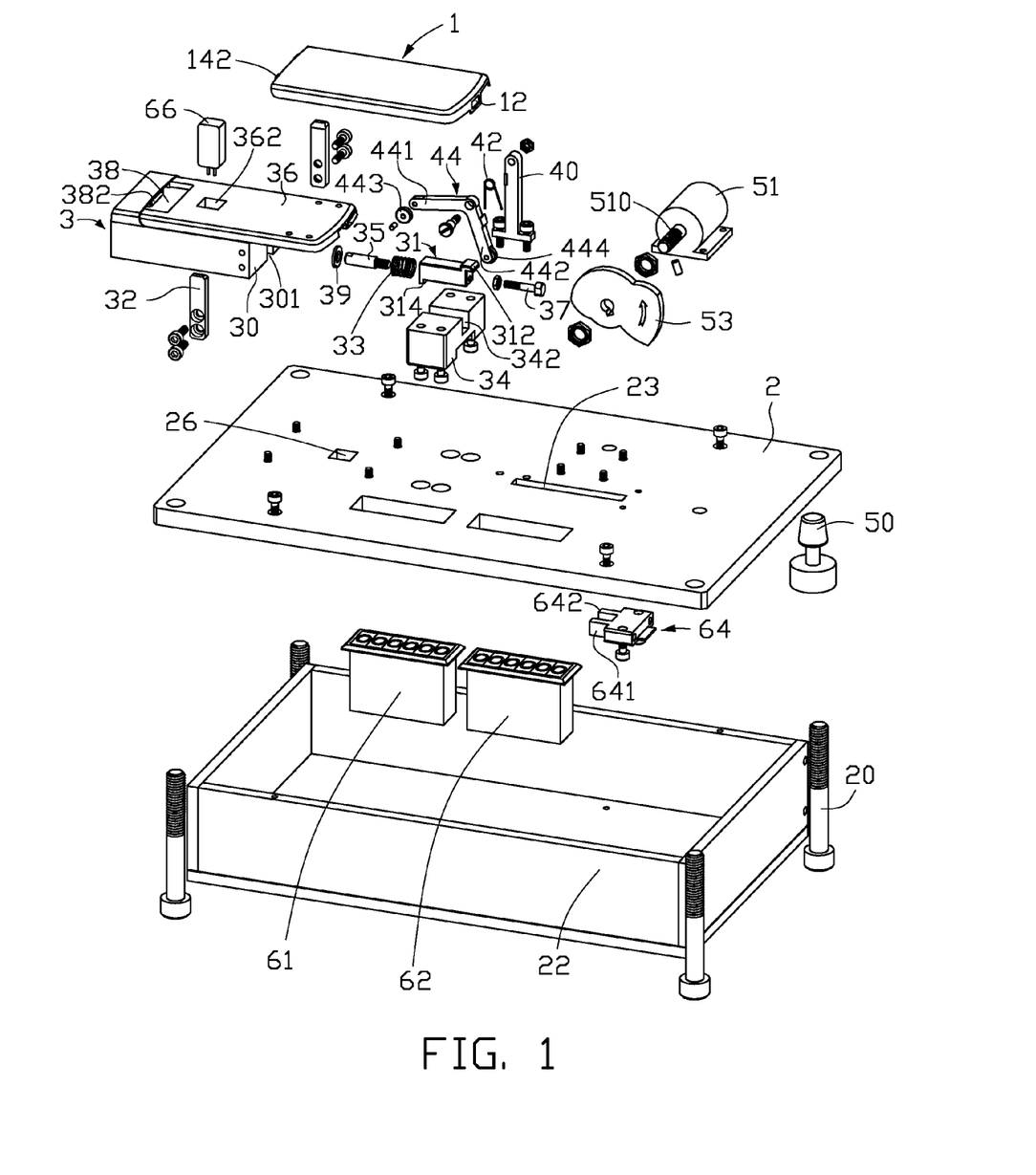
FIG. 1 is an exploded, isometric view of an exemplary embodiment of a testing apparatus, together with a cover of a mobile phone to be tested.
Figure 2:
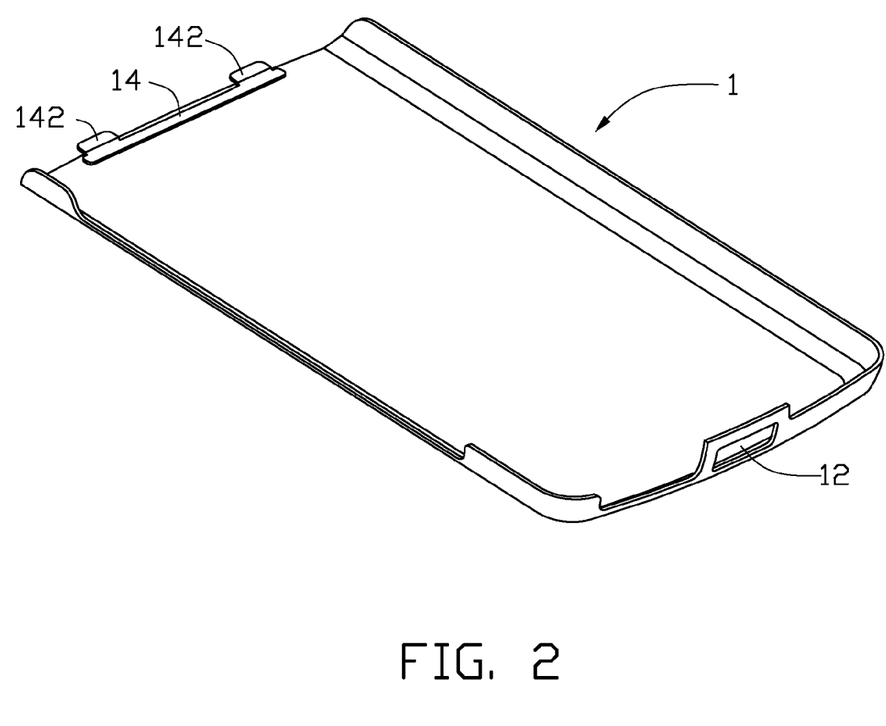
FIG. 2 is an isometric, inverted view of the cover of FIG. 1.
Figure 3:
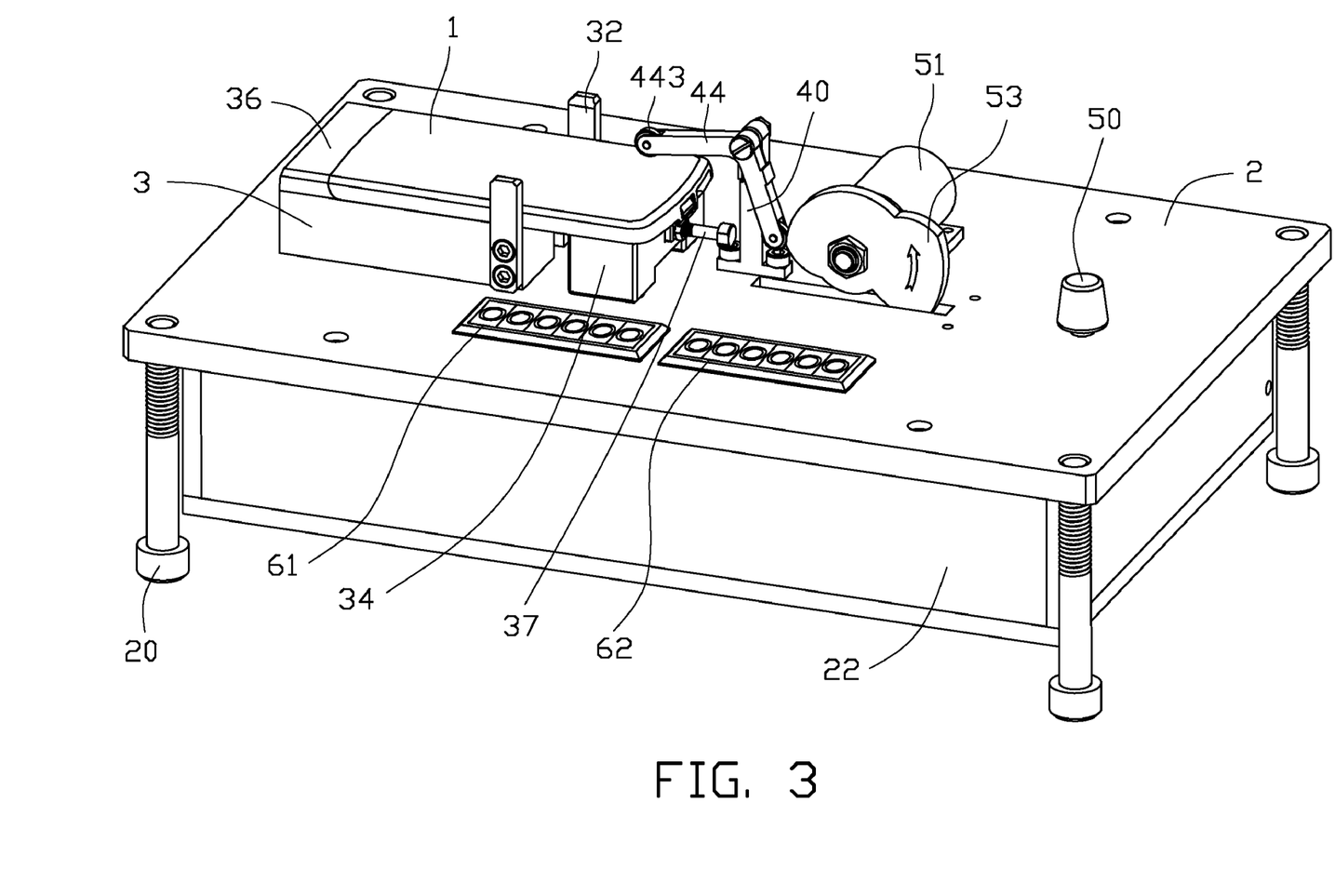
FIG. 3 is an assembled, isometric view of the testing apparatus and the cover of FIG. 1.

Referring to FIGS. 1 through 3, an exemplary embodiment of a testing apparatus is shown to be used to test mechanical endurance of a cover 1 of a mobile phone (not shown).

The cover 1 includes a clipping ring 12 formed at a first end of the cover 1, and a hinge 14 extending from a second end of the cover 1 opposite to the first end. The hinge 14 includes two projections 142 extending from the hinge 14 at both ends thereof. During the use of the mobile phone, the clipping ring 12 may break due to repeated clipping, and same for the hinge 14 due to repeatedly folding and unfolding. The clipping ring 12 and the hinge 14 are mechanically weak portions of the cover. Thus, the clipping ring 12 and the hinge 14 need to be tested to determine the mechanical endurance of the cover 1.

The testing apparatus includes a worktable 2, a mechanism (not label), an electrical device (not label), a box 22 attached to a bottom of the worktable 2, and four bolts 20 configured for supporting the worktable 2. The mechanism is generally placed over the worktable 2. The electrical device is placed under the worktable 2.

The mechanism includes an imitator device for imitating work actions (such as clipping and hinging) of the cover 1, and a movement circulator (not label) for causing the cover 1 work repeatedly.

The imitator device includes an installing member 3 fixed to the worktable 2 adjacent to a first end of the worktable 2, two restricting blocks 32 fixed to opposite sides of the installing member 3, a guiding block 34 fixed to the worktable 2 adjacent to an end wall 30 at a second end of the installing member 3, and a clipping imitator (not labeled) slidably supported on the guiding block 34.

Figure 4:
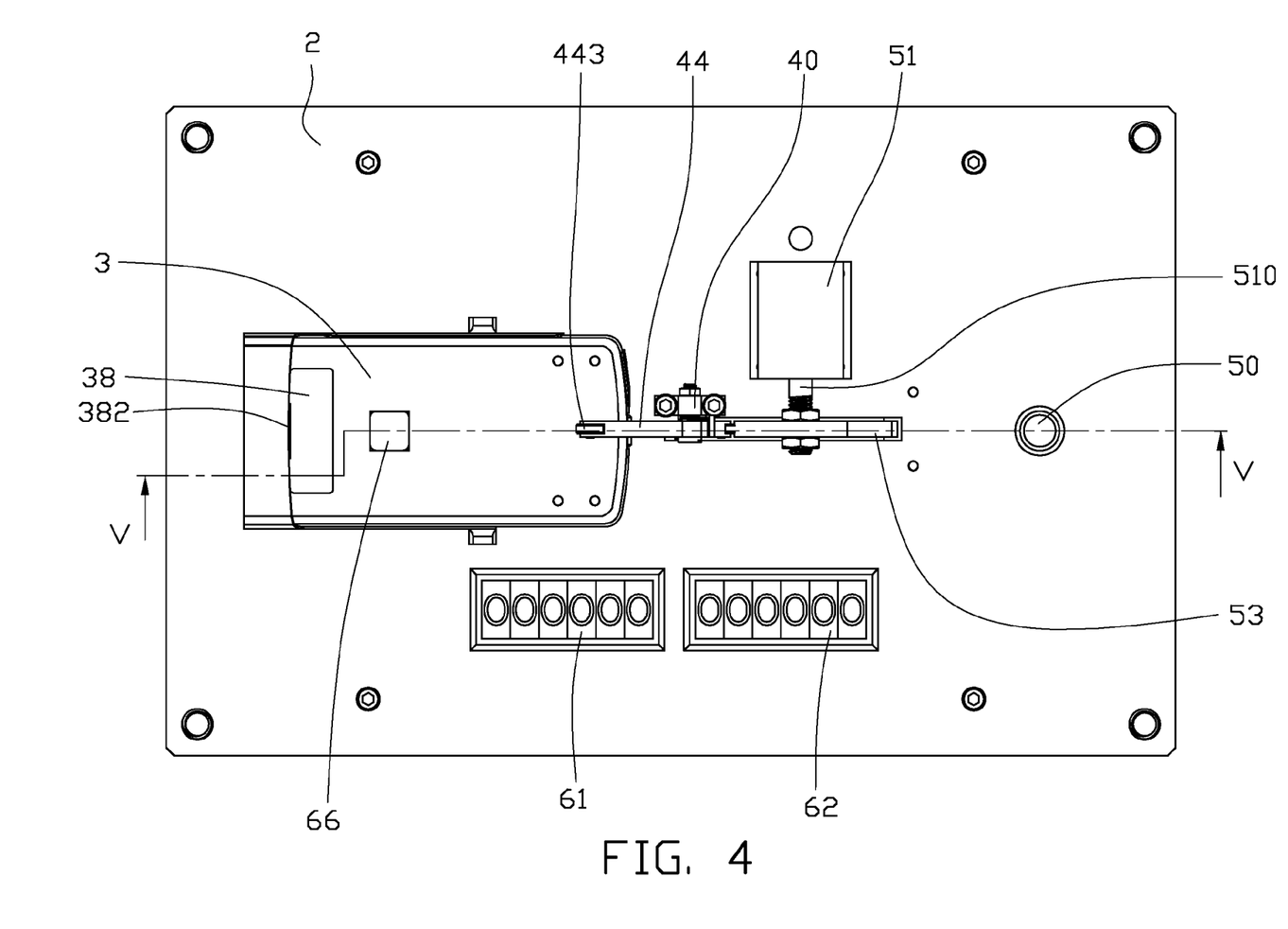
FIG. 4 is a top plan view of FIG. 3, except that the cover of the mobile pone is omitted.
Figure 5:
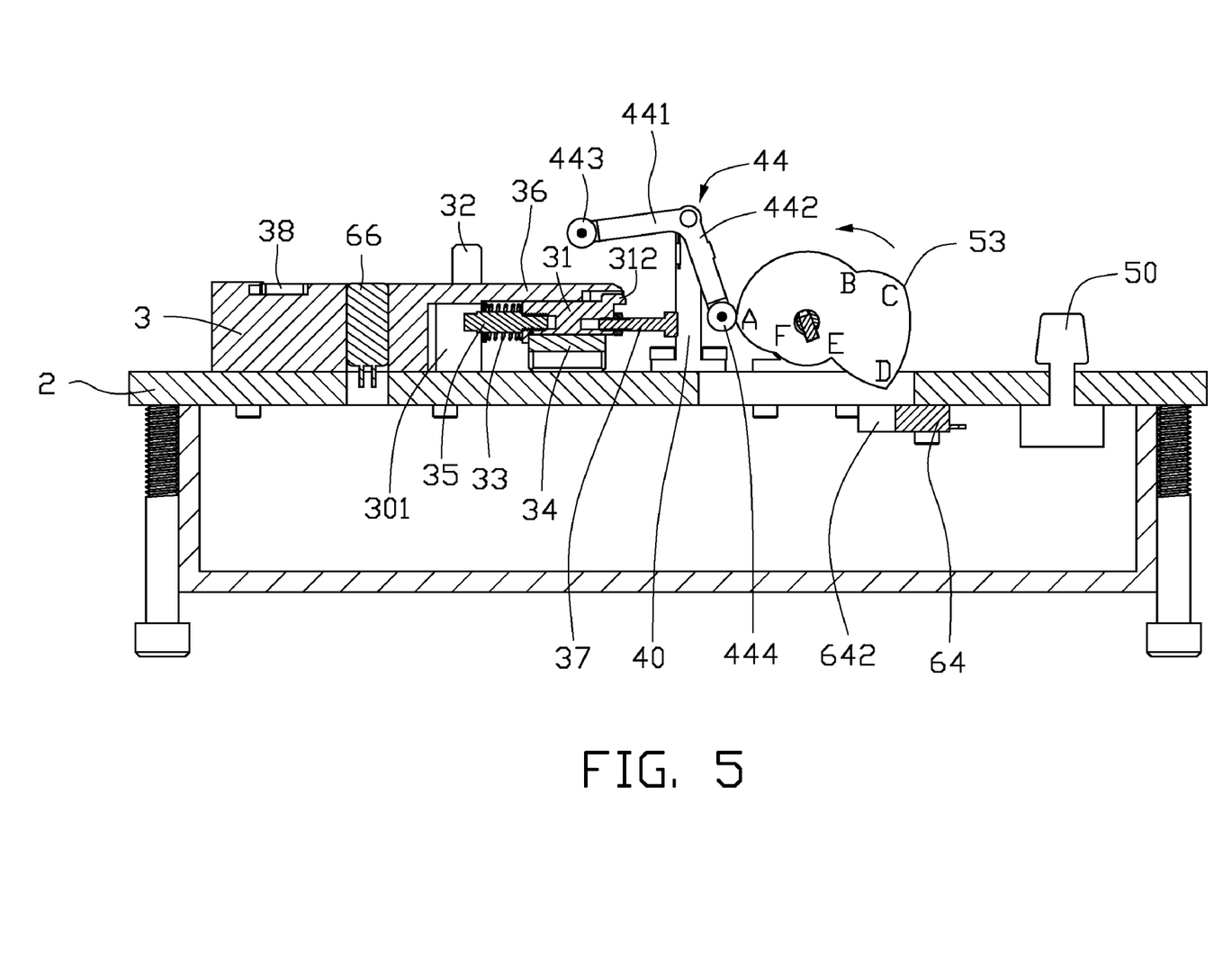
FIG. 5 is a cross-sectional view of FIG. 4, taken along the line V-V in FIG. 4.
Figure 6:
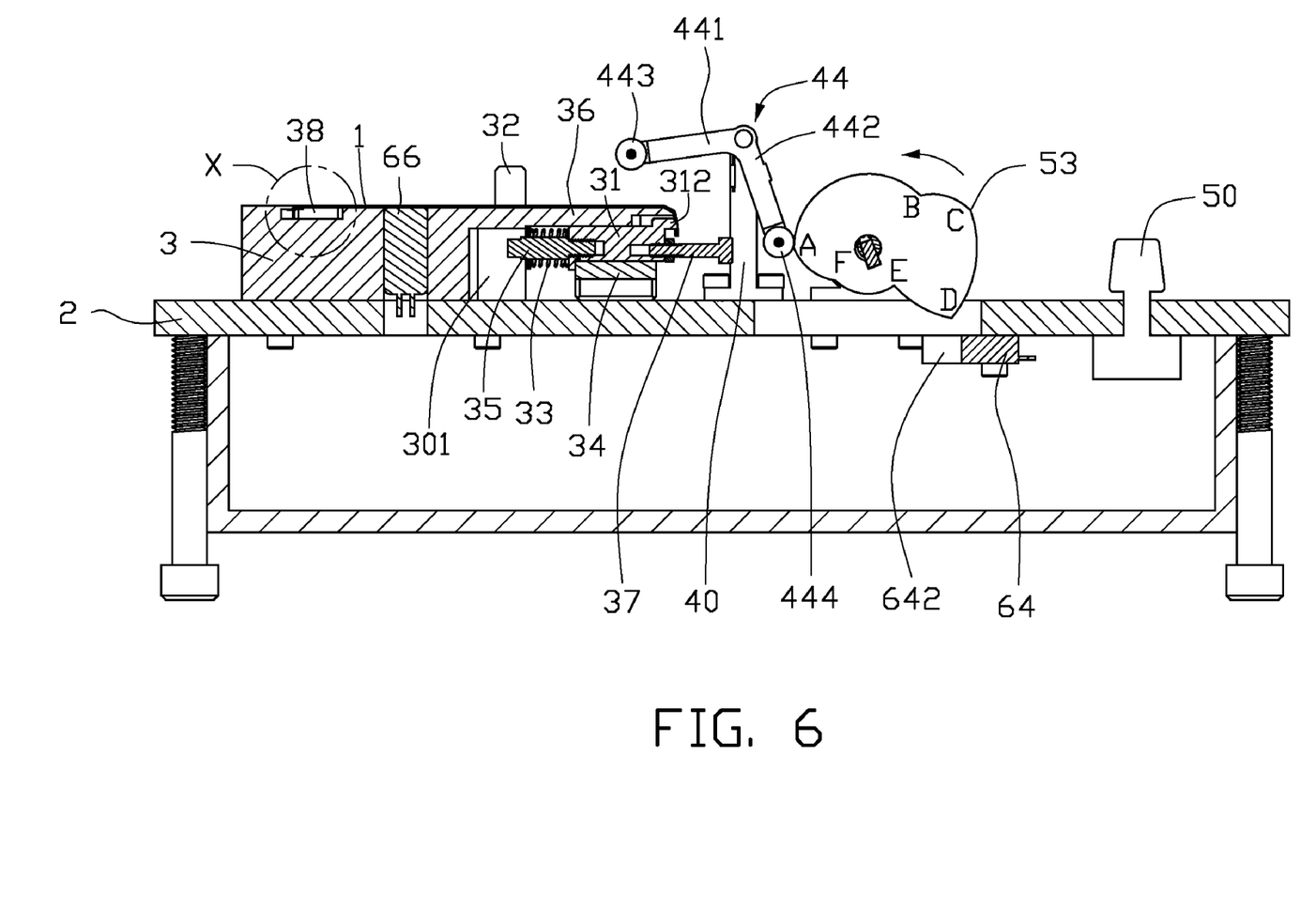
FIGS. 6-9 are similar to FIG. 5, except that the cover of the mobile phone is shown and in different states.
Figure 10:
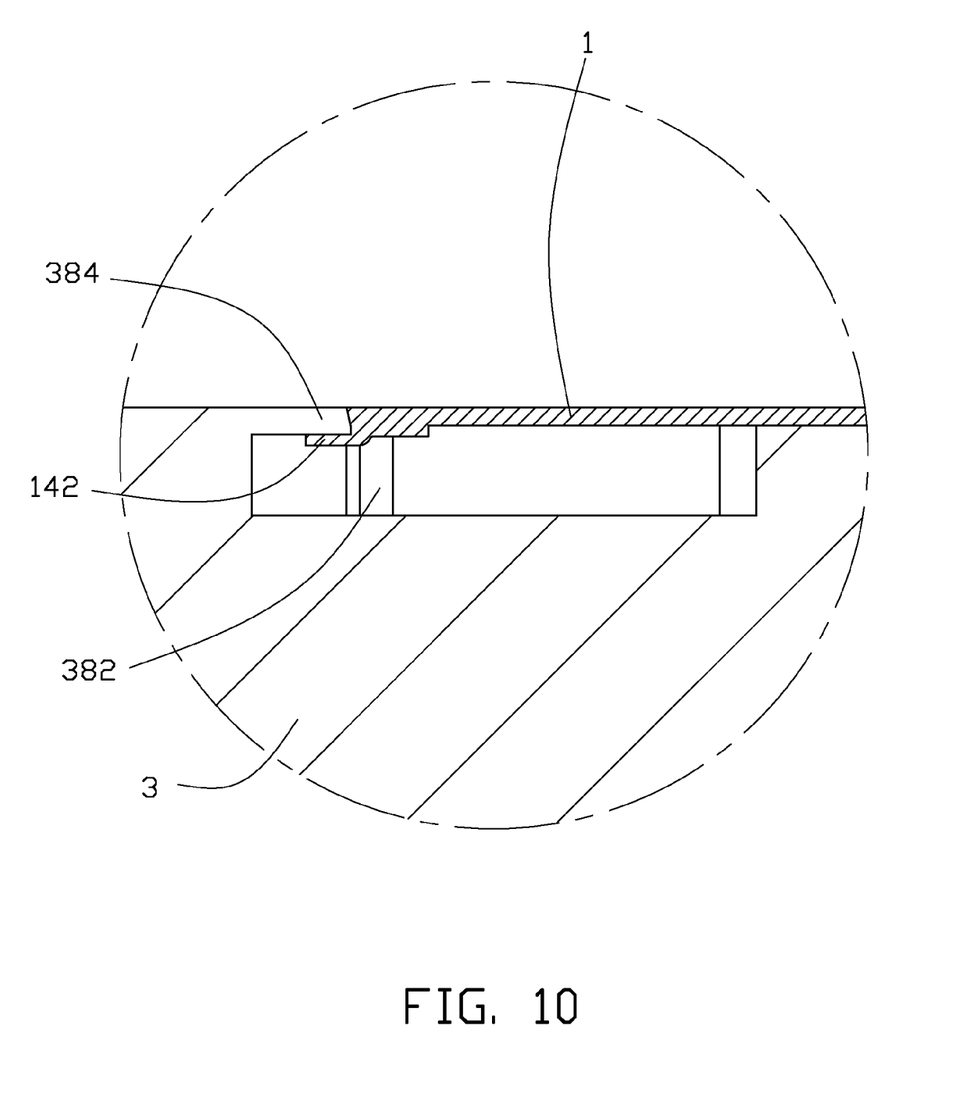
FIG. 10 is an enlarged view of the circled portion X of FIG. 6.

Referring to FIGS. 4 through 6, the installing member 3 includes a cantilever plate 36 extending out of the end wall 30 and over the guiding block 34. The cover 1 is installed on the installing member 3 and restricted between the two restricting blocks 32. A depressed portion 38 is defined in a top of the installing member 3 near the first end. A hinging imitator (not labeled) is formed in the depressed portion 38. The hinging imitator includes a support 382, and a pressing piece 384 (see FIG. 10 for details). When the cover 1 is installed on the installing member 3, the projections 142 of the cover 1 are pressed down by the pressing piece 384, and roots of the projections 142 are supported by the support 382, resulting in the cover 1 tending to rotate relative to the support 382. Referring to FIG. 1 again, a through hole 362 is defined in the installing member 3, extending through the top and the bottom of the installing member 3. A slot 301 is defined in the end wall 30 of the installing member 3, under the cantilever plate 36.

A groove 342 is defined in the guiding block 34.

The clipping imitator includes a sliding block 31, an elastic member such as a coiled spring 33, a first elongated portion 35, a second elongated portion 37, and a gasket 39. The sliding block 31 is slidably received in the groove 342 of the guiding block 34, and includes an L-shaped clipping tongue 312 extending from a top of a first end of the sliding block 31, and a blocking piece 314 extending down from a second end of the sliding block 31. The blocking piece 314 resists against a first end wall of the guiding block 34, to prevent the sliding block 31 from sliding out of the groove 342 through a second end wall of the guiding block 34, wherein the first end wall of the guiding block 34 facing the end wall 30 of the installing member 3. The first elongated portion 35 is fixed to the first end wall of the sliding block 31 via threaded connection. The second elongated portion 37 is fixed to the second end wall of the sliding block 31 via threaded connection. A free end of the first elongated portion 35 extends through the coiled spring 33 and the gasket 39, and extends into the slot 301 of the installing member 3. Two ends of the coiled spring 33 abut against the first end wall of the sliding block 31 and the gasket 39, pushing the gasket 39 against the end wall 30 of the installing member 3. When the cover 1 is installed on the installing member 3, the clipping tongue 312 is extended through and engaged with the clipping ring 12.

The movement circulator includes an oscillating device (not label), a drive device (not label), and a speeder 50.

The oscillating device includes a rod holder 40 fixed to the worktable 2 and located adjacent to the second end wall of the guiding block 34, an oscillating rod 44 rotatably attached to the rod holder 40, and an elastic member such as a torsion spring 42 mounted between the rod holder 40 and the oscillating rod 44. The oscillating rod 44 is capable of rotating while under the force of the torsion spring 42. The oscillating rod 44 includes a first arm 441, and a second arm 442 that is not aligned with the first arm 441. The first arm 441 includes a first wheel 443 attached to a free end of the first arm 441. The second arm 442 includes a second wheel 444 attached to a free end of the second arm 442.

The drive device includes a motor 51, and a cam 53. The motor 51 is fixed to the worktable 2 and located at a side away from the guiding block 34 of the rod holder 40. The motor 51 includes a power shaft 510. The cam 53 is fixed to the power shaft 510 and is capable of rotating with the power shaft 510. A profile of the cam 53 engages with the second wheel 444, thus driving the oscillating rod 44 to rotate reciprocally, in other words, the oscillating rod 44 is the follower of the cam 53. The profile of the cam 53 includes six trace points A, B, C, D, E, and F as shown in FIG. 5 which divide the profile of the cam 53 into six curves: a near dwell curve EF between the trace points E and F, a first rise curve FA between the trace points F and A, a middle dwell curve AB between the trace points A and B, a second rise curve BC between the trace points B and C, a far dwell curve CD between the trace points C and D, and a return curve DE between the trace points D and E. An avoiding hole 23 is defined in the worktable 2. The cam 53 can be partly inserted through the avoiding hole 23 when rotating.

The speeder 50 is installed to the worktable 2, configured for controlling the speed of the motor 51.

Figure 11:
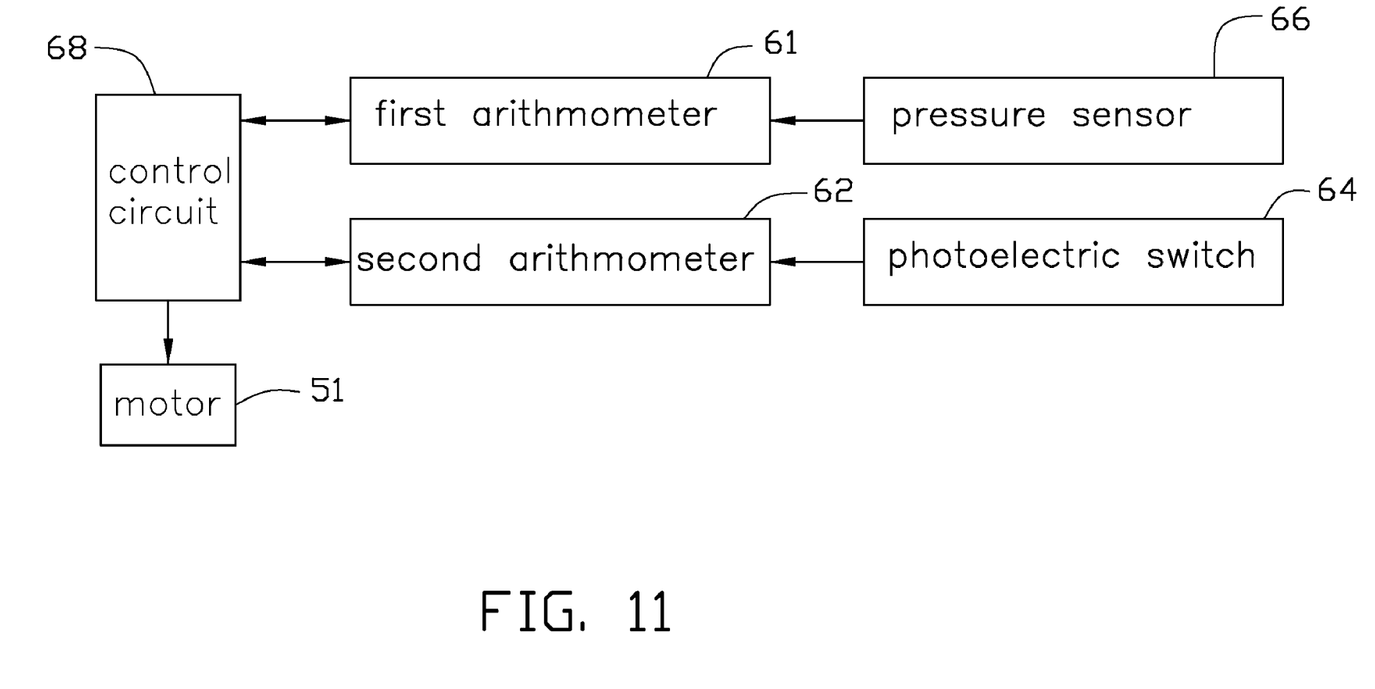
FIG. 11 is a block diagram of the testing apparatus of FIG. 3.

Referring also to FIG. 11, the electrical device includes a pressure sensor 66, a first arithmometer 61, a photoelectric switch 64, a second arithmometer 62, and a control circuit 68. The first arithmometer 61, the photoelectric switch 64, the second arithmometer 62, and the control circuit 68 are received in the box 22.

The pressure sensor 66 is received in the through hole 362 of the installing member 3. A top of the pressure sensor 66 extends out of the through hole 362 a little, so as to receive a pressure of the installed cover 1.

The first arithmometer 61 is electrically connected to the pressure sensor 66 via an electrical wire (not shown). The first arithmometer 61 is capable of recording a count of pressure dropping that the pressure sensor 66 detects.

The photoelectric switch 64 includes an emitter 641, and a receiver 642. Light is emitted by the emitter 641 and received by the receiver 642. The photoelectric switch 64 is placed under the cam 53, and is set to allow only the far dwell curve CD to be able to enter between the emitter 641 and the receiver 642 so as to cut off the light path, so that only the far dwell curve CD of the cam 53 can change the photoelectric switch 64 to be in an off state. Thus, in each rotation cycle of the cam 53, the photoelectric switch 64 turns to be in off state once.

The second arithmometer 62 is electrically connected to the photoelectric switch 64, and is configured to record a count the photoelectric switch 64 being in off state.

Referring to FIG. 6, the cover 1 is installed on the installing member 3, with the projections 142 inserted under the pressing piece 384 and supported on the support 382 of the installing member 3, and the clipping ring 12 fitting about the clipping tongue 312 of the sliding block 31. When the motor 51 is started the cam 53 is rotated anticlockwise. In a rotation cycle of the cam 53, if the cover 1 does not break, the mechanism will perform the following.

(a) When the oscillating rod 44 follows the middle dwell curve AB of the cam 53 via the second wheel 444 thereof, the oscillating rod 44 touches the cam 53 but does not touch the cover 1, the torsion spring 42 between the rod holder 40 and the oscillating rod 44 is deformed, and the cover 1 applies pressure on the pressure sensor 66.

Figure 7:
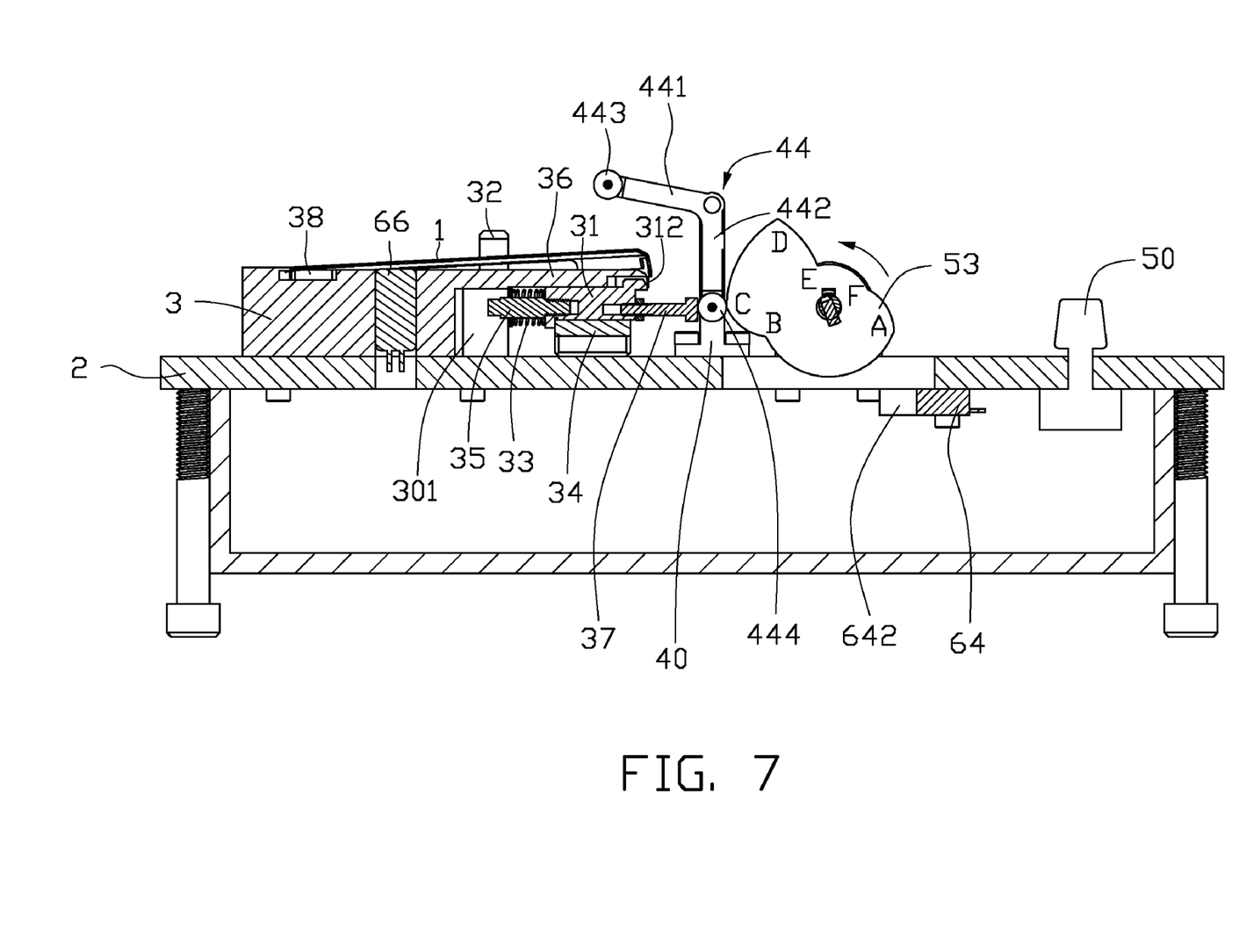

(b) Referring to FIG. 7, when the oscillating rod 44 follows the second rise curve BC, the second arm 442 is pushed by the cam 53 to move toward the second elongated portion 37, driving the oscillating rod 44 to rotate relative to the rod holder 40, and resulting in the first arm 441 moving upward and away from the cover 1. When the second wheel 444 touches the second elongated portion 37, the sliding block 31 is driven to slide toward the end wall 30 of the installing member 3. The torsion spring 42 is further deformed, and the coil spring 33 is deformed. When the second wheel 444 reaches to the trace point C as shown in FIG. 7, the clipping tongue 312 of the sliding block 31 disengages from the clipping ring 12 of the cover 1. Because the projections 142 of the cover 1 are pressed down by the pressing piece 384 and the roots of the projections 142 are supported by the support 382, the cover 1 rotates relative to the support 382 after the clipping tongue 312 disengaging from the clipping ring 12, resulting in the first end of the cover 1 tilting upwards to release pressure from the pressure sensor 66. In fact, the cover 1 continues applying pressure on the pressure sensor 66 due to gravity, however, sensitivity of the pressure sensor 66 can be adjusted to counter gravity influence. When the oscillating rod 44 follows the far dwell curve CD, the clipping imitator and the cover 1 remain at the above-mentioned states when the second wheel 444 reaches to the trace point C.

Figure 8:
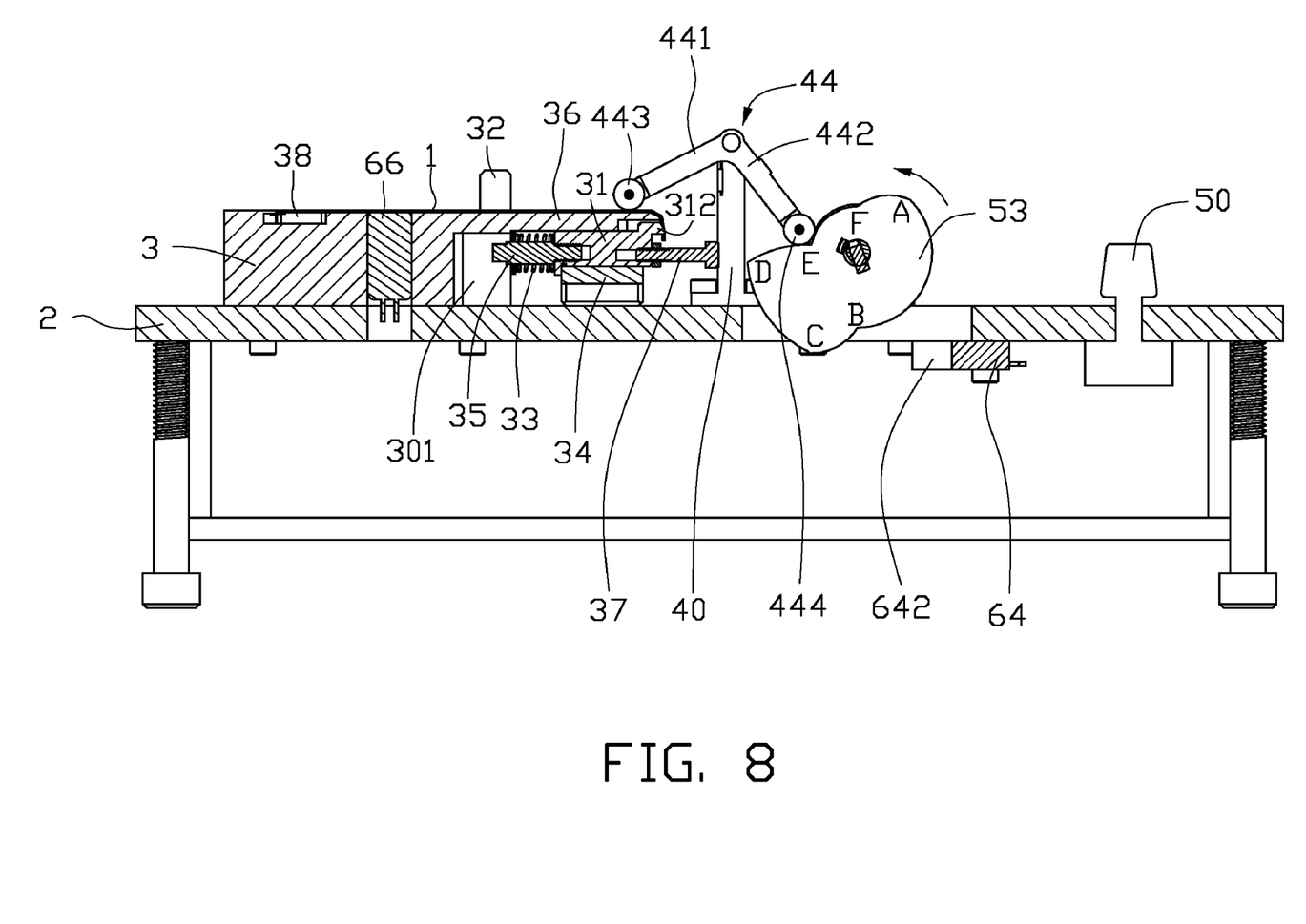

(c) Referring to FIG. 8, when the oscillating rod 44 follows the return curve DE, the torsion spring 42 biases the second arm 442 to rotate away from the second elongated portion 37 and the first arm 441 move toward the cover 1. The second wheel 444 is disengaged from the second elongated portion 37, the coil spring 33 biases the sliding block 31 to slide back. The first wheel 443 of the first arm 441 presses the cover 1 downwards, the clipping tongue 312 is engaged in the clipping ring 12. The cover 1 applies pressure on the pressure sensor 66 again. After that, when the oscillating rod 44 follows the near dwell curve EF, the clipping imitator and the cover 1 remain at the above-mentioned states when the oscillating rod 44 follows the return curve DE.

(d) Referring to FIG. 6 again, when the oscillating rod 44 follows the first rise curve FA, the second arm 442 is pushed by the cam 53 to move toward the second elongated portion 37 but not touching the second elongated portion 37, and the first arm 441 moves upward thereby disengaging from the cover 1. After that, the oscillating rod 44 will follow the middle dwell curve AB again to enter into a next rotation cycle.

According to what is described above, during a rotation cycle of the cam 53, if the cover 1 does not break, the pressure sensor 66 will lose pressure only once when the oscillating rod 44 follows the far dwell curve CD.

Figure 9:
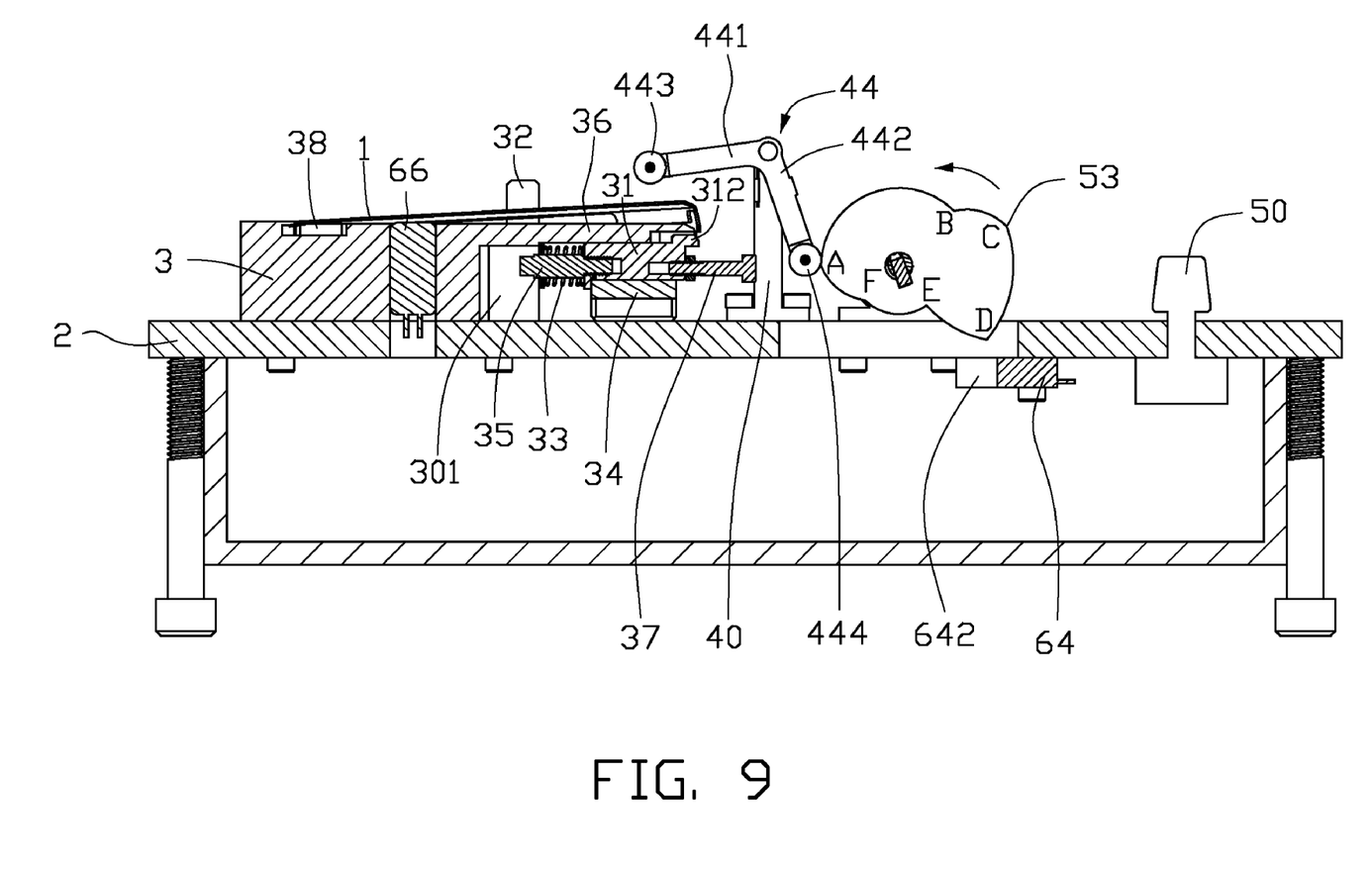

If the clipping ring 12 or the hinge 14 of the cover 1 breaks during a certain rotation cycle of the cam 53, the cover 1 will tilt upward because of the broken clipping ring 12, or the rotation tendency of the cover 1 will disappear because of the broken hinge 14, resulting in the pressure sensor 66 detecting that pressure drops twice. Referring to FIGS. 8 and 9, and comparing FIG. 9 with FIG. 6, take the clipping ring 12 as an example. If the clipping ring 12 does not broken, when the oscillating rod 44 follows the near dwell curve EF, the pressure sensor 66 receives pressure of the first arm 441 applying on the cover 1, and when the second wheel 444 rolls along the middle dwell curve AB, the pressure sensor 66 receives pressure of the cover 1 (see FIG. 6). However, if the clipping ring 12 breaks, when the oscillating rod 44 follows the near dwell curve EF, the pressure sensor 66 receives pressure of the first arm 441 applying on the cover 1, but when the oscillating rod 44 follows the middle dwell curve AB, the first end of the cover 1 tilts upward resulting in the pressure sensor 66 losing pressure (see FIG. 9). Thus, in this rotation cycle, the pressure sensor 66 loses pressure twice when the oscillating rod 44 follows the far dwell curve CD (see FIG. 7) and the near dwell curve EF.

Referring to FIG. 11, when the testing apparatus is started, the control circuit 68 controls the motor 51 to spin and reset the arithmometers 61, 62. The first arithmometer 61 takes count of pressure dropping that the pressure sensor 66 detects. The second arithmometer 62 takes count of being in off state of the photoelectric switch 64, namely takes count of number of turns of the cam 53. The control circuit 68 receives and compares count data from the arithmometers 61, 62 in each rotation cycle of the cam 53. If the count of the first arithmometer 61 equals to the count of the second arithmometer 62, the control circuit 68 controls the motor 51 to keep on spinning. If the count of the first arithmometer 61 is different from the count of the second arithmometer 62, the control circuit 68 controls the motor 51 to stop. Suppose that the cam 53 is in the Nth rotation cycle, and the clipping ring 12 or the hinge 14 of the cover 1 breaks. According to the hereinbefore description, the count of the second arithmometer 62 should be N, the count of the first arithmometer 61 should be N+1, and the motor 51 stops spinning. Thus, according to the count of the second arithmometer 62, the mechanical endurance of the cover 1 can be known, in other words, the clipping ring 12 or the hinge 14 of the cover 1 can be used N times before breaking.

Generally, the clipping ring 12 is mechanically weaker than the hinge 14, so the present testing apparatus is often used to test the clipping ring 12 only.

In other embodiments, the near dwell curve EF, the middle dwell curve AB, and the far dwell curve CD may be omitted, because these omitted curves are generally used to supply buffering action, in other words, they supply standstill period for the oscillating rod 44.

It is believed that the present embodiments and their advantages is understood from the foregoing description, and it will be apparent that various changes may be made thereto without departing from the spirit and scope of the embodiments or sacrificing all of their material advantages, the examples hereinbefore described merely being exemplary embodiments of the invention.

What is claimed is:

1. A testing apparatus for testing mechanical endurance of a workpiece that has a clipping ring extending from a first end thereof and a hinge extending from a second end thereof, the testing apparatus comprising:
    a worktable;
    an installing member mounted on the worktable and configured for installing the workpiece;
    a clipping imitator configured for clipping the clipping ring of the workpiece;
    a hinging imitator configured for engaging with the hinge of the workpiece and making the workpiece tend to rotate relative to the hinge when the workpiece is installed on the installing member;
    a cam mounted on the worktable and capable of rotating periodically;
    an oscillating rod configured for following the cam, the oscillating rod comprising a first arm and a second arm extending from the first arm, wherein the second arm contacts with and follows the cam, and is capable of impelling the clipping imitator to detach from the clipping ring, the first arm is capable of pressing the workpiece toward the installing member;
    a pressure sensor capable of receiving pressure from the workpiece when the workpiece lying on the installing member;
    a first arithmometer configured for recording a count of pressure dropping that the pressure sensor detects; and
    a second arithmometer configured for taking count of number of turns of the cam;
    wherein in a rotation cycle of the cam, if the workpiece dose not breaks, the count of the first arithmometer equals to the count of the second arithmometer; if the workpiece breaks, the count of the first arithmometer is different from the count of the second arithmometer.

2. The testing apparatus of claim 1, wherein the cam comprises a first rise curve, a second rise curve, and a return curve;
    when the oscillating rod follows the first rise curve, the second arm moves toward the clipping imitator, and the first arm disengages and moves away from the workpiece;
    when the oscillating rod follows the second rise curve, the second arm further moves toward the clipping imitator, and then pushes the clipping imitator to detach from the clipping ring; and
    when the oscillating rod follows the return curve, the first arm moves toward the workpiece and then presses the workpiece down, the second arm disengages from the clipping imitator, and the clipping imitator engages with the clipping ring.

3. The testing apparatus of claim 2, wherein the cam further comprises a near dwell curve between the return curve and the first rise curve.

4. The testing apparatus of claim 2, wherein the cam further comprises a middle dwell curve between the first rise curve and the second rise curve.

5. The testing apparatus of claim 2, wherein the cam further comprises a far dwell curve between the second rise curve and the return curve.

6. The testing apparatus of claim 5, further comprising a photoelectric switch, wherein the photoelectric switch is set to allow only the far dwell curve of the cam to be able to change the photoelectric switch to be in off state in a rotation cycle of the cam; the second arithmometer takes count of number of turns of the cam via recording a count of being in off state of the photoelectric switch.

7. The testing apparatus of claim 1, further comprising a motor mounted on the worktable and configured for driving the cam to rotate.

8. The testing apparatus of claim 7, further comprising a control circuit configured for controlling the motor, and receiving and comparing count data from the first arithmometer and second arithmometer.

9. The testing apparatus of claim 7, further comprising a speeder button configured for adjusting the speed of the motor.

10. The testing apparatus of claim 1, wherein the installing member defines a hole, the pressure sensor is received in the hole, a top surface of the pressure sensor extends out of the hole so as to receive the pressure from the workpiece.

11. The testing apparatus of claim 1, wherein the clipping imitator comprises a guiding block defining a groove, a sliding block slidably received in the groove, and an elastic member sandwiched between the sliding block and the installing member to bias the sliding block; the sliding block comprises a clipping tongue configured for engaging with the clipping ring.

12. The testing apparatus of claim 11, wherein the elastic member is a coil spring, the sliding block comprises an elongated portion, the installing member defines a slot in an end wall thereof, the coil spring fits about the elongated portion, the elongated portion is capable of extending in the slot when the sliding block slides.

13. The testing apparatus of claim 11, wherein the sliding block comprises a blocking piece configured to prevent the sliding block from sliding out of the groove.

14. The testing apparatus of claim 1, wherein a depressed portion is defined in the installing member, the hinging imitator is formed in the depressed portion, the hinging imitator includes a support, and a pressing piece, wherein when the workpiece is installed on the installing member, the hinge is pressed down by the pressing piece and a root of the hinge is supported by the support, so that the workpiece tends to rotate relative to the support.

15. The testing apparatus of claim 1, further comprising a rod holder mounted on the worktable and an elastic member, wherein the oscillating rod is rotatably attached to the rod holder; the elastic member is sandwiched between the rod holder and the oscillating rod for biasing the oscillating rod.

16. The testing apparatus of claim 15, wherein the elastic member is a torsion spring.

17. The testing apparatus of claim 1, wherein the first arm comprises a wheel attached to a free end thereof for touching the workpiece.

18. The testing apparatus of claim 1, wherein the second arm comprises a wheel attached to a free end thereof for engaging with the cam and the clipping imitator.

* * * * *